US010342553B2

(12) United States Patent
Gilhooley

(10) Patent No.: US 10,342,553 B2
(45) Date of Patent: Jul. 9, 2019

(54) SURGICAL SAGITTAL SAW AND COMPLEMENTARY BLADE WITH FEATURES THAT FIXEDLY HOLD THE BLADE STATIC TO THE SAW

(71) Applicant: Stryker European Holdings I, LLC, Kalamazoo, MI (US)

(72) Inventor: Seamus Gilhooley, Athenry (IE)

(73) Assignee: Stryker European Holdings I, LLC, Kalamazoo, MI (US)

(*) Notice: Subject to any disclaimer, the term of this patent is extended or adjusted under 35 U.S.C. 154(b) by 501 days.

(21) Appl. No.: 14/997,720

(22) Filed: Jan. 18, 2016

(65) Prior Publication Data
US 2016/0206326 A1 Jul. 21, 2016

Related U.S. Application Data

(60) Provisional application No. 62/105,795, filed on Jan. 21, 2015.

(51) Int. Cl.
*A61B 17/14* (2006.01)
*A61B 17/16* (2006.01)
*A61F 2/46* (2006.01)
*B23D 51/10* (2006.01)
*B23D 61/00* (2006.01)
*B23D 61/12* (2006.01)

(52) U.S. Cl.
CPC ........ *A61B 17/1637* (2013.01); *A61B 17/142* (2016.11); *A61F 2/4609* (2013.01); *B23D 51/10* (2013.01); *B23D 61/006* (2013.01); *B23D 61/123* (2013.01); *A61F 2002/4619* (2013.01)

(58) Field of Classification Search
CPC . A61B 17/1637; A61B 17/142; A61F 2/4609; A61F 2002/4619; B23D 51/10; B23D 61/006; B23D 61/123
USPC ...................................... 606/167–179, 79–82
See application file for complete search history.

(56) References Cited

U.S. PATENT DOCUMENTS

| 2,547,707 A | 4/1951 | Karle |
| 2,854,981 A | 10/1958 | Morrison |
| 3,554,197 A | 1/1971 | Dobbie |
| 3,678,934 A | 7/1972 | Warfield et al. |

(Continued)

FOREIGN PATENT DOCUMENTS

| DE | 8631778 U1 | 2/1987 |
| DE | 3640516 C1 | 4/1988 |

(Continued)

OTHER PUBLICATIONS

Machine-assisted English translation for DE 86 31 778 extracted from espacenet.com database on Dec. 14, 2017, 8 pages.

(Continued)

*Primary Examiner* — Zade Coley
*Assistant Examiner* — Jessica Weiss
(74) *Attorney, Agent, or Firm* — Howard & Howard Attorneys PLLC

(57) ABSTRACT

A surgical sagittal saw with a complementary blade. The blade is formed with a void to receive a pin associated with the saw that releasably holds the blade to the saw. The blade and the pin have complementary tapered surfaces. When the tapered surface of the pin moves against the tapered surface of the blade, the blade is urged against a static surface of the saw.

17 Claims, 10 Drawing Sheets

(56) References Cited

U.S. PATENT DOCUMENTS

| | | | |
|---|---|---|---|
| 3,852,881 A | 12/1974 | Treace | |
| 3,905,105 A | 9/1975 | Tuke | |
| 3,952,412 A | 4/1976 | Rhodes | |
| 3,964,163 A | 6/1976 | Russo | |
| 3,978,862 A | 9/1976 | Morrison | |
| 4,020,555 A | 5/1977 | Hedrick | |
| 4,106,181 A | 8/1978 | Mattchen | |
| 4,252,121 A | 2/1981 | Arnegger | |
| 4,386,609 A | 6/1983 | Mongeon | |
| 4,768,504 A | 9/1988 | Ender | |
| 4,922,612 A | 5/1990 | Greenwood | |
| 5,042,983 A | 8/1991 | Rayhack | |
| 5,092,869 A | 3/1992 | Waldron | |
| 5,201,749 A | 4/1993 | Sachse et al. | |
| 5,340,129 A | 8/1994 | Wright | |
| 5,366,312 A | 11/1994 | Raines | |
| 5,468,247 A | 11/1995 | Matthai et al. | |
| 5,489,285 A | 2/1996 | Gods | |
| 5,505,738 A | 4/1996 | Hempel et al. | |
| 5,554,165 A | 9/1996 | Raitt et al. | |
| 5,569,257 A | 10/1996 | Arnegger et al. | |
| 5,609,603 A | 3/1997 | Linden | |
| 5,846,244 A | 12/1998 | Cripe | |
| 5,916,218 A | 6/1999 | Hagen et al. | |
| 6,007,541 A | 12/1999 | Scott | |
| 6,113,618 A | 9/2000 | Nic | |
| 6,302,406 B1 | 10/2001 | Ventura | |
| 6,485,495 B1 | 11/2002 | Jenkinson | |
| 6,857,348 B1 | 2/2005 | Mason | |
| 7,704,254 B2 | 4/2010 | Walen | |
| 8,100,912 B2 | 1/2012 | Marietta | |
| 2002/0116007 A1 | 8/2002 | Lewis | |
| 2002/0116023 A1 | 8/2002 | Fletcher et al. | |
| 2002/0133185 A1 | 9/2002 | Danger et al. | |
| 2002/0133186 A1 | 9/2002 | Kullmer | |
| 2003/0199880 A1 | 10/2003 | Meckel | |
| 2004/0098000 A1* | 5/2004 | Kleinwaechter | B23D 61/006 |
| | | | D24/146 |
| 2004/0138668 A1 | 7/2004 | Fisher et al. | |
| 2004/0204731 A1 | 10/2004 | Gant | |
| 2005/0192585 A1 | 9/2005 | Simmons | |
| 2006/0009796 A1 | 1/2006 | Carusillo et al. | |
| 2006/0053639 A1 | 3/2006 | Nakanishi | |
| 2007/0119055 A1 | 5/2007 | Walen et al. | |
| 2007/0123893 A1* | 5/2007 | O'Donoghue | A61B 17/142 |
| | | | 606/82 |
| 2008/0027449 A1 | 1/2008 | Gundlapalli et al. | |
| 2009/0182338 A1 | 7/2009 | Walen et al. | |
| 2009/0312761 A1 | 12/2009 | Boykin et al. | |
| 2009/0312762 A1 | 12/2009 | Boykin | |
| 2009/0312779 A1 | 12/2009 | Boykin et al. | |
| 2010/0281695 A1 | 11/2010 | Nie | |
| 2010/0292701 A1 | 11/2010 | Fisher et al. | |
| 2011/0046627 A1 | 2/2011 | Kim | |
| 2011/0092975 A1 | 4/2011 | Fisher et al. | |
| 2012/0041443 A1 | 2/2012 | Landon | |
| 2013/0204255 A1* | 8/2013 | Milburn | A61B 17/142 |
| | | | 606/82 |
| 2013/0204256 A1* | 8/2013 | Wang | B27B 5/32 |
| | | | 606/82 |
| 2014/0015207 A1* | 1/2014 | Kaye, Jr. | B25F 3/00 |
| | | | 279/143 |
| 2014/0018811 A1 | 1/2014 | Mootien et al. | |
| 2014/0182872 A1 | 7/2014 | Rubens et al. | |
| 2015/0359641 A1 | 12/2015 | Nic | |
| 2016/0100846 A1 | 4/2016 | Motherway et al. | |
| 2016/0206326 A1 | 7/2016 | Gilhooley | |

FOREIGN PATENT DOCUMENTS

| | | |
|---|---|---|
| DE | 29810157 U1 | 8/1998 |
| DE | 20012138 U1 | 12/2000 |
| DE | 202006009423 U1 | 8/2006 |
| DE | 202008017023 U1 | 3/2009 |
| DE | 202011000681 U1 | 6/2011 |
| DE | 202011052439 U1 | 1/2012 |
| DE | 102011056927 A1 | 6/2013 |
| EP | 1529612 A1 | 5/2005 |
| EP | 1974881 A2 | 10/2008 |
| EP | 2502579 A1 | 9/2012 |
| GB | 2463351 A | 3/2010 |
| WO | 2010129243 A2 | 11/2010 |
| WO | 2012170459 A2 | 12/2012 |
| WO | 2013016472 A1 | 1/2013 |
| WO | WO-2014/207552 * | 12/2014 ............. A61B 17/16 |

OTHER PUBLICATIONS

English language abstract and machine-assisted English translation for DE 36 40 516 extracted from espacenet.com database on Dec. 14, 2017, 6 pages.

Machine-assisted English translation for DE 298 10 157 extracted from espacenet.com database on Dec. 14, 2017, 19 pages.

Machine-assisted English translation for DE 200 12 138 extracted from espacenet.com database on Dec. 14, 2017, 7 pages.

English language abstract and machine-assisted English translation for DE 20 2006 009 423 extracted from espacenet.com database on Dec. 14, 2017, 9 pages.

Machine-assisted English translation for DE 20 2008 017 023 extracted from espacenet.com database on Dec. 14, 2017, 28 pages.

Machine-assisted English translation for DE 20 2011 000 681 extracted from espacenet.com database on Dec. 14, 2017, 12 pages.

Machine-assisted English translation for DE 20 2011 052 439 extracted from espacenet.com database on Dec. 14, 2017, 20 pages.

English language abstract and machine-assisted English translation for DE 10 2011 056 927 extracted from espacenet.com database on Dec. 14, 2017, 22 pages.

English language abstract and machine-assisted English translation for EP 197 48 81 extracted from espacenet.com database on Dec. 14, 2017, 13 pages.

English language abstract and machine-assisted English translation for EP 250 25 79 extracted from espacenet.com database on Dec. 14, 2017, 13 pages.

* cited by examiner

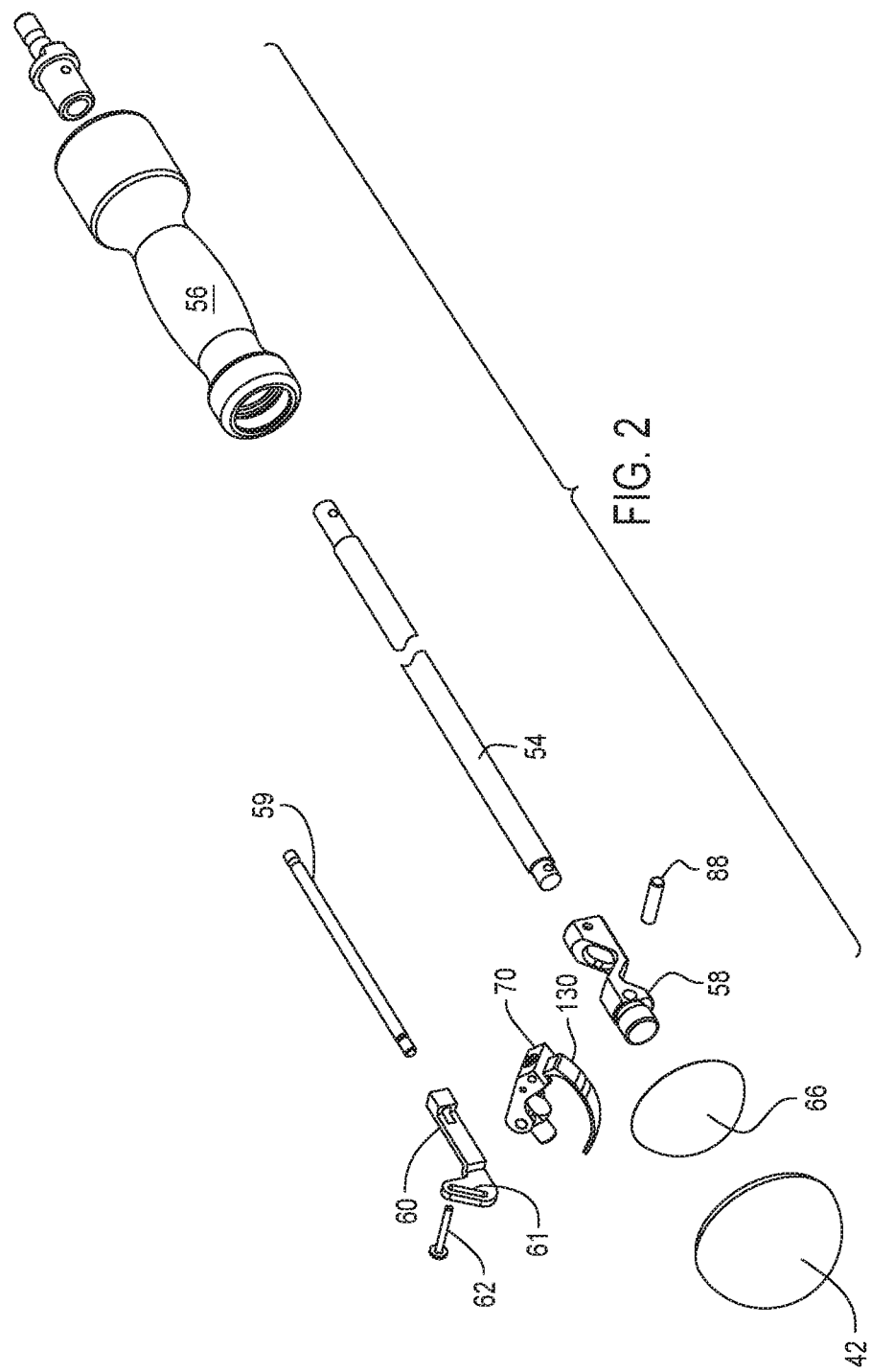

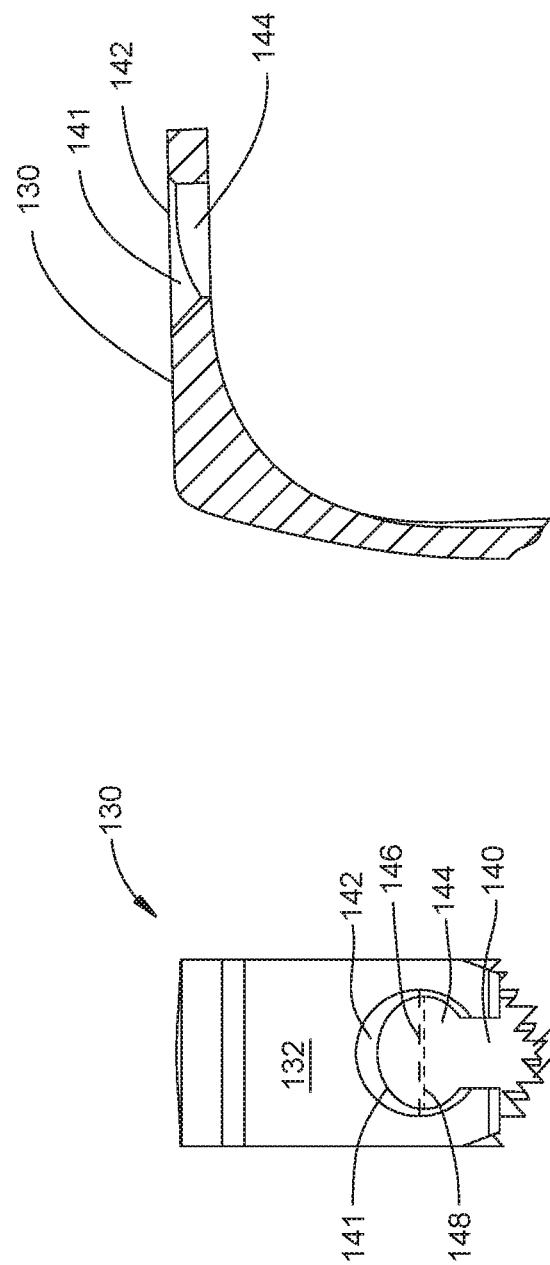

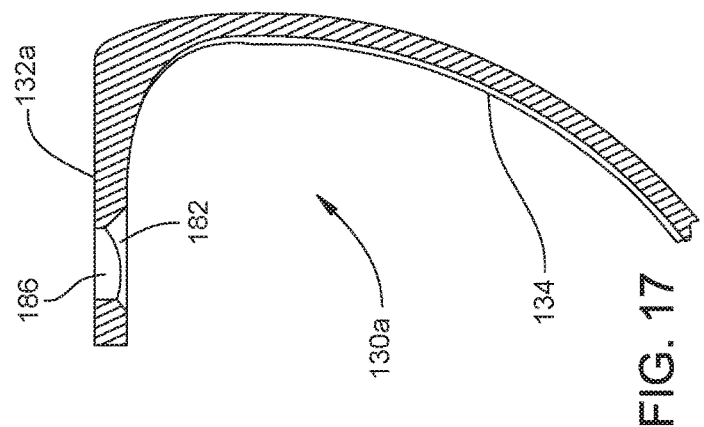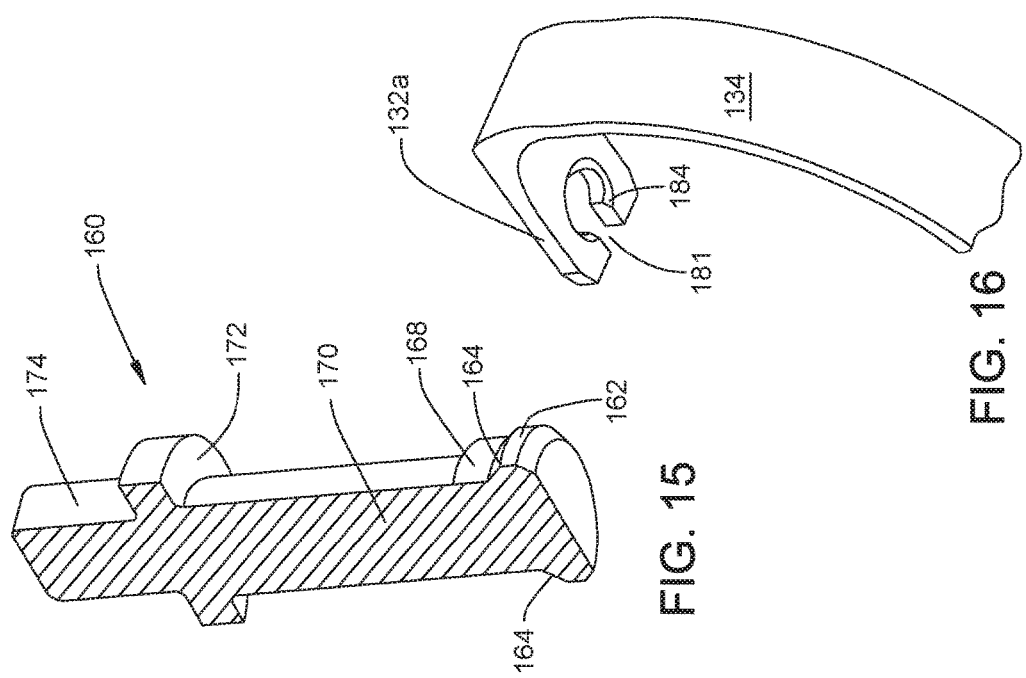

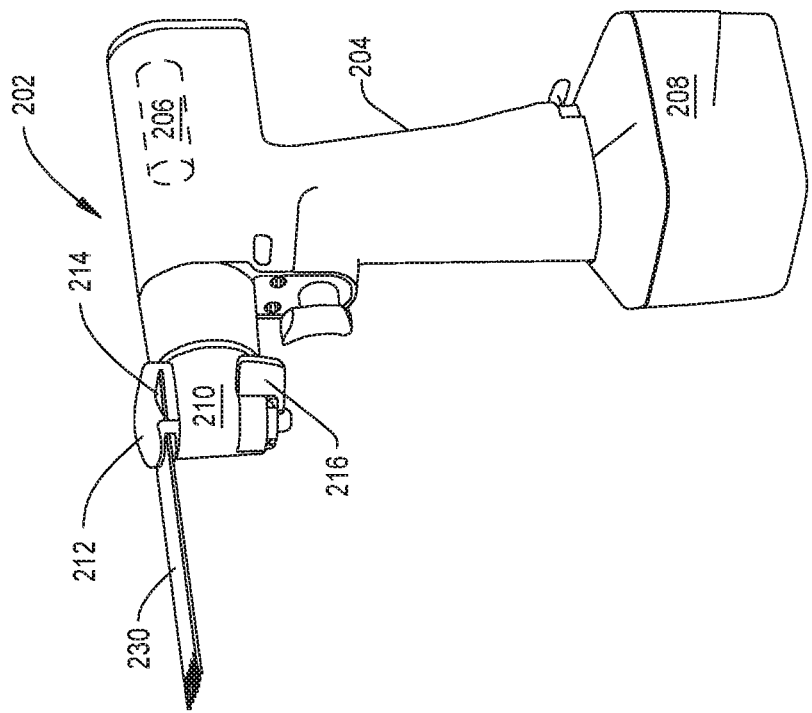

SURGICAL SAGITTAL SAW AND COMPLEMENTARY BLADE WITH FEATURES THAT FIXEDLY HOLD THE BLADE STATIC TO THE SAW

FIELD OF THE INVENTION

This invention generally relates to surgical sagittal saws and the complementary blades used with the sagittal saws. The invention relates to a saw and blade with complementary features that facilitate holding the blade static to the saw at a fixed location relative to the saw.

BACKGROUND OF THE INVENTION

A powered surgical instrument, surgical tool, used with some frequency is the powered surgical saw. This type of instrument is used to remove tissue, including bone and cartilage. Attached to the saw is a saw blade. A drive assembly internal to the saw reciprocates the blade in a back and forth motion. Often the saw includes a moving head. The head is the component of the saw to which the blade is mounted. Some blades are constructed to pivot back and forth, oscillate, in the plane in which the blade is oriented. This type of blade is referred to as a sagittal saw blade. A sagittal saw blade is provided with teeth that extend forward from the distal end of the blade body.

Many sagittal saws and their complementary blades are designed so that the blade extends distally forward of the blade head. One such assembly is disclosed in the Applicant's U.S. Pat. No. 8,100,912/PCT Pub. No. WO 2007/011542, the contents of which are incorporated herein by reference. This type of saw and blade is used to remove a section of bone. This is the most common type of sagittal saw.

A species of the sagittal saw is the acetabular cup remover. As implied by its name, this type of surgical power instrument is used to remove an artificial acetabular cup. An artificial acetabular cup is sometimes implanted in a patient during hip replacement surgery. Hip replacement surgery consists of the replacement of the existing ball and socket of the hip joint with prosthetic replacements. The head of the femur, the ball, is typically removed and replaced with a femoral component made of biocompatible material. This component mirrors the structure of the original bone. The acetabulum, the socket in the hip, is often reamed to form a hole. An artificial acetabular cup that corresponds and cooperates with the femoral component is fitted in the hole. This artificial acetabular cup often includes an outer shell constructed of a metallic material. Typically this shell is in the form of a hollowed out semi-sphere. An insert, constructed of plastic, ceramic or metal, is seated in the outer shell. In many cases, the acetabular cup component is anchored in the bone with cement. Some cups are press fit in place. Still other cups are held in place by screws or fastening tabs integral with the cup itself. A combination of these fastening methods may be employed. Sometimes, owing to the shape of the outer shell and/or the application of compound that enhance bone growth, the outer shell is designed to foster the growth of bone adjacent the shell. This new bone anchors the cup to the rest of the hip. Total hip replacement surgery has often proven successful in relieving many problems associated with the hip joint.

Total hip replacement surgery is often successful. Nevertheless, it is sometimes necessary to perform the same surgery on the same hip. This may be necessary in situations in which wear or infection degrade the performance of the installed cup and femoral head. This sub-set of total hip replacement surgery is sometimes called revision surgery. In a revision surgery, it is necessary to remove the acetabular cup previously implanted in the hip. As mentioned above, these components may have been cemented in place or otherwise held by bone or fibrous tissue that may have grown in and around the component. Thus, their removal requires the cutting or chipping away of cement or bone material.

The acetabular cup remover is employed to remove the artificial acetabular cup. This type of saw includes a pivot head that seats in the socket of the cup. A saw head is connected to the pivot head. The complementary blade has a foot that projects outwardly from the head. The blade has a trunk, a main body, that, relative to the foot, extends downwardly. More particularly, the trunk is shaped to curve around the outer surface of the cup the saw is employed to remove. Teeth extend outwardly from the end and sometimes the side of the trunk. When this type of saw is actuated, the saw head is oscillated to cause a similar back and forth motion of the blade. The blade is then driven around the outer surface of the cup. As a consequence of the oscillatory movement and the blade being simultaneously driven around the cup, the blades, cuts, chips away, bone and any cement that holds the cup to the bone. PCT Pub. No. WO 2014/133536/US Pat. Pub. No. US 2015/0359641 A and PCT Pub. No. WO 2014/207552/US Pat. Pub. No. 2016/0100846 A1, both of which are explicitly incorporated herein by reference, disclose an acetabular cup remover and a number of different blades that can be used with this type of saw.

A surgical sagittal includes an assembly for removably holding the blade to the saw head. This is because the blade, to ensure sterility is removed and replaced between surgeries on different patients. Often a new blade is used for each surgery. This is because upon use of the blade, the teeth are immediately dulled. Owing to the economics, it is often more cost effective to use a new blade with each patient than go to the expense of sterilizing and resharpening previously used blade. This means that each time a saw or acetabular cup remover is used for a new patient, a new blade is fitted to the saw. Moreover, during the process of removing acetabular cup, often two or more blades are used in sequence. The first blade has a trunk that subtends a first arc. This blade is used to form an initial shallow cut around the acetabular cup being removed. Once this shallow cut is formed, a second blade is fitted to the acetabular cup remover. This second blade subtends an arc greater than that subtended by the first blade. The second blade is used to form a deeper cut. This deeper cut typically extends completely around the cup. Once this deep cut is formed, the cup is then removed from the hip.

A surgical sagittal, include a saw designed as an acetabular cup remover, is typically designed so that the head has a slot. The slot is the void space dimensioned to receive the proximal end of the blade. Often the proximal end of the blade is provided with one or more openings. Each opening is dimensioned to receive a pin that is moveably mounted to the saw head. The seating of the pin the blade opening releasably holds the blade to the head.

It is common practice to collectively dimension the saw head and blade so the slot allows the close slip fitting of the blade in the slot. This slip fit dimensioning facilitates the relatively easy insertion of the blade into and removal of the blade from the saw head. An inevitable amount of this component dimensioning is that within the slot, there is small clearance between the blade and the interior surfaces of the saw head that define the slot. This means that within the slot the blade has some space to move.

Owing to this tendency of the blade to move within the slot, the back-and-forth movement of the blade is not always in phase with the back-and-forth movement of the saw head. More specifically this occurs because when the saw head reverses direction, owing to the blade having a momentum in the opposite direction, the blade continues to move in the first direction. Thus, there may be times in the movement of the saw head and blade where these two components move in the opposed directions. This can result in the blade striking an adjacent surface of the saw head. This action is sometimes referred to as blade slap. A result of blades continually slapping against the saw head is that the material forming the head can fatigue. This component fatigue can result in the fracturing of the saw head. Once such a fracture occurs, at a minimum, it is necessary to replace the saw head.

This movement of the blade relative to the saw head can also result in the blade moving to a less than optimal position for the procedure being performed. When a conventional sagittal saw is used, the blade is often placed in a resection guide. A resection guide is a block that is affixed to the bone adjacent where the cut is to be formed. The block is formed with one or more slots. The slots serve as guide paths through which the saw blade is inserted. By cutting the bone along the guide paths defined by the slots, the surgeon shapes the remaining bone to have a selected, precisely defined shape. This precision shaping of the bone is often performed to ensure the proper fitting of an orthopedic implant to the bone. Owing to the flexure of the blade when fitted in one of these slots, the blade can gall, wear the material that defines the slots. This can result in the shape of the slot deforming from the shape needed to ensure that a cut formed based on the shape of the slot has the desired shape. Once this deformation of the resection guide occurs, the guide is no longer useful.

This blade shifting is also disadvantageous when it occurs relative to the head of an acetabular cup remover. This is because the acetabular cup remover is designed so that when the blade is fitted to the saw, and the blade moved around the cup being removed, the blade ideally should move as close as possible around the cup without pressing against the cup. If the blade is spaced away from the cup, more bone is removed from the patient than is necessary to remove the acetabular cup. This can complicate the process of fitting the replacement cup. If the blade presses against the acetabular cup the metal-against-metal movement of the blade, at a minimum, reduces the efficiency of the bone removal process. A more adverse result from this contact is the deformation of the blade or the cup. Either of these events can appreciably complicate the removal of the old cup and the fitting of the replacement cup.

There is therefore a desire to provide a surgical sagittal saw and complementary blade that are constructed so that, when the saw and blade are actuated, the saw head and blade move as a single rigid structure. A means to satisfy this design objective is to design the saw head and blade so the blade is compression fit in the saw head. This can be impracticable because it can require the use of force to first insert the blade into the saw head and then to remove the blade from the head. Having to employ this kind of force can slow the blade removal and insertion processes. Further, the teeth of these blades are very sharp. To reduce the likelihood that the individual tasked with blade insertion and blade removal inadvertently cut himself/herself on the teeth, it might be desirable for this individual task to use a tool to apply the force. The need to provide this type of force with a tool can further complicate the processes of inserting and removing the blades.

An alternative means to ensure the saw head and blade move as a single rigid body is to provide a clamping assembly that, when set, applies an appreciable amount of force to the blade to hold the blade to the saw head. This typically means that the individual charged with blade insertion and blade removal apply a significant amount of force to reset and release the clamping assembly. Requiring the individual responsible to perform these tasks to apply these forces can complicate the process of inserting and removing the blade. This is especially true if the individual has limited arm and hand strength. Further, if these forces are not properly applied, especially the force required to set the clamping assembly, the blade may not be fully locked to the saw head. When the saw is actuated this could result in a clearly undesirable event, the blade working free from the saw.

SUMMARY OF THE INVENTION

This invention relates to a new and useful surgical saw with a coupling assembly that firmly, yet releasably, holds the complementary blade to the saw head so the saw head and blade essentially move as a single component. This invention also relates to a surgical saw blade designed for use with the saw of this invention.

This invention further relates to a new and useful surgical sagittal saw that, when the blade is held to the saw, though releasably attached to the saw, abuts a static surface of the saw head to which the blade is attached. This invention also relates to a surgical sagittal saw blade designed for use with the saw of this invention.

The saw of this invention includes a head to which the blade is attached. The head is formed with a slot for receiving the blade. A pin is moveably mounted to the head and extends through the slot. The portion of the pin that extends through the slot includes a neck that, relative to a longitudinal axis of the pin, defines a cross section that is non-circular in shape. In many versions of the invention, the neck has major and minor axis of different lengths. The major axis is longer in length than the minor axis.

In many versions of the invention, the pin has a shoulders that emerge from the neck. The shoulders taper outwardly to a circular waist. In some versions of the invention, the waist has a diameter equal to the major diameter of the pin neck.

The blade is formed to define voids that are complementary to the pin neck and shoulder. One of these voids is an opening. The opening is formed with a taper or bevel that is complementary to the taper of the shoulders. Often, but not always, the opening is circular in shape. The opening opens into a through hole that extends through the blade. The through hole has a non-circular shape that is complementary to the non-circular shape of the pin neck. The blade through hole is typically formed with a major axis and shorter minor axis.

In many versions of the invention, the diameter across the blade opening is not in registration with the major axis across the blade through hole. In many preferred versions of the invention, the blade is shaped so the axis along the diameter of the opening is located distally forward of the major axis across the through hole. In other words the center of the opening is located distally forward of the center of the through hole.

In some versions of the invention, the pin neck and complementary blade through hole are at least partially curved in shape. In some more preferred versions of the invention the pin neck and complementary blade through hole are, elliptical in shape.

In some versions of invention, relative to gravity, the saw head and complementary pin are shaped so that the blade opening extends downwardly into the blade through hole. In other versions of the invention, relative to gravity, the components are constructed so that the blade opening extends upwardly from an undersurface, an underside face, of the blade into the blade through hole.

BRIEF DESCRIPTION OF THE DRAWINGS

The invention is pointed out with particularity in the claims. The above and further features and benefits of this invention are understood from the following Detailed Description taken in conjunction with the accompanying drawings in which:

FIG. 2 is an exploded view of the distal end components of the acetabular cup remover;

FIG. 11 is a top plan view of the saw blade;

FIG. 12 is a cross sectional view of the saw blade of FIG. 11;

FIG. 15 is a cross sectional and perspective view of the moving pin internal to the saw head of FIG. 13;

FIG. 16 is a perspective view of a portion of the blade of FIG. 13;

FIG. 17 is a cross sectional view of a portion of the blade of FIG. 13;

FIG. 18 is an alternative sagittal saw that incorporates the features of this invention; and FIG. 19 is a plan view of a blade for use with the saw of FIG. 18.

DETAILED DESCRIPTION

Figure 1:
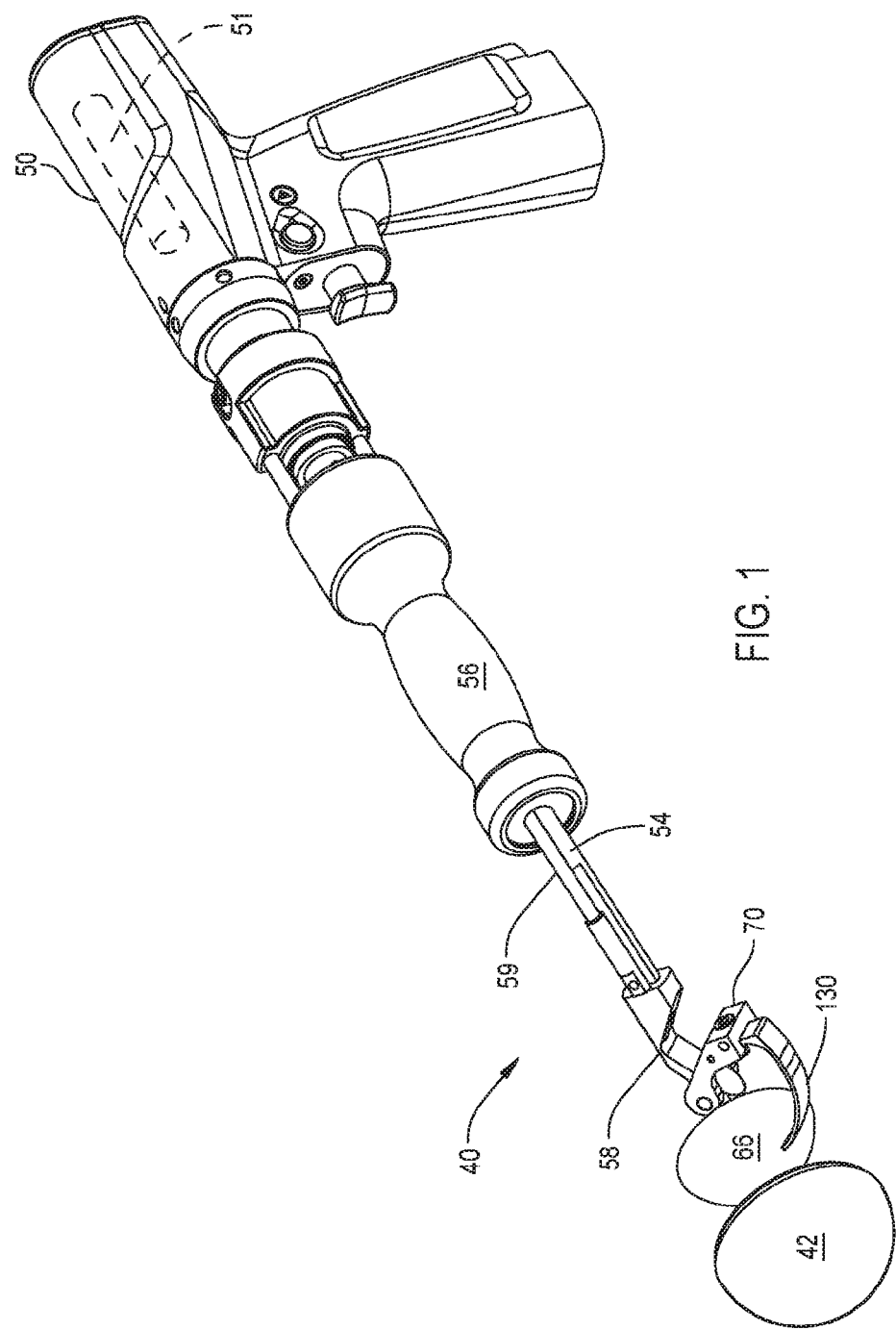
FIG. 1 is a perspective view of a sagittal saw, specifically an acetabular cup remover, that includes the head and blade of this invention.

FIGS. 1 and 2 illustrate a type of a surgical sagittal saw, an acetabular cup remover 40, of this invention and the relation of the tool to an acetabular cup 42. The cup 42 is often in the form of a hollow semi-spherical structure typically formed of metal. The outer surface of the cup 42 is embedded in the bone of the hip. The inner surface of the cup 42 defines a socket (not illustrated). This socket is designed to receive the ball of a femoral stem. While not illustrated, a liner, often in the form of a hollow semi-spherical structure, may be seated against the inner surface of the cup 42. The liner, when present, defines the socket space that receives the femoral ball.

The cup remover 30 includes a pivot head 66. Pivot head 66 is the portion of the cup remover 30 that is seated in the cup 42. A coupler 58 extends proximally away from the head. The coupler 58 is an elongated structure. ("Proximally," it is understood means towards the surgeon using the cup remover 40, away from the cup 42. "Distally" means away from the surgeon, towards the cup 42.) A shaft 54 extends proximally from the distal end of the coupler 58. A saw head 70 is connected to the coupler so as to be located less than 4 cm proximally away to where the coupler extends away from the cup. The saw head 70 is pivotally connected to the coupler 58. For this reason, saw head 70 of an acetabular cup remover is sometimes referred to as a hinge. A blade 130 is removably attached to and extends outwardly from the saw head. Blade 130 is shaped so, when the saw head 70 is pivoted in the forward direction, the blade extends around the outer surface of the cup 42.

A handle 56 is slidably connected to the shaft 54 at a location slightly forward of the proximal end of the shaft. An actuator rod 59 is located adjacent to and extends distally forward with the shaft 54. The proximal end of the actuator rod 58 is connected to the handle 56 so that the rod moves with the handle. An actuator 60 is connected to the distal end of the actuator rod. Actuator 60 is formed to have an elongated slot 61. The actuator 60 is shaped so that as slot 61 extends proximally, the slot extends outwardly from the longitudinal axis of the actuator 60. A pin 62 that extends through slot 61 connects the actuator 60 to the saw head 70. The longitudinally movement of the handle 56 over the shaft 54 results in the like longitudinal movement of the actuator rod 59 and actuator 60 relative to the shaft 54. The longitudinal movement of the actuator 60 causes the saw head 70 to pivot. This pivoting is around and axis that is perpendicular to the longitudinal axis of the actuator rod 59. The pivoting of the saw head 70 results in the blade 130 being pivoted either distally forward, against the bone surrounding the acetabular cup 42 or proximally, away from this tissue.

The proximal end of the shaft 54 is attached to a driver 50. The driver 50 is a surgical handpiece. Internal to the driver is a motor 51, represented as a phantom cylinder. When the driver 50 is actuated, the driver rotates the shaft 54 and by extension, the components attached to the shaft. These components include the blade 130. In many versions of the invention, the driver 50 is configured so that when the driver is actuated, the driver oscillates the shaft 54 back and forth around the longitudinal axis of the shaft. When the shaft 54 is oscillated while the saw head 70 is in the forward position, the movement of the shaft results in the blade 130 being driven back and forth against the bone against which the blade is pressed.

The exact structure of the driver, the shaft and the mechanism that pivots the saw head is not part of the present invention. The incorporated by reference PCT Pub. No. WO 2014/133536 provides a more detailed understanding of these components.

Figure 4:
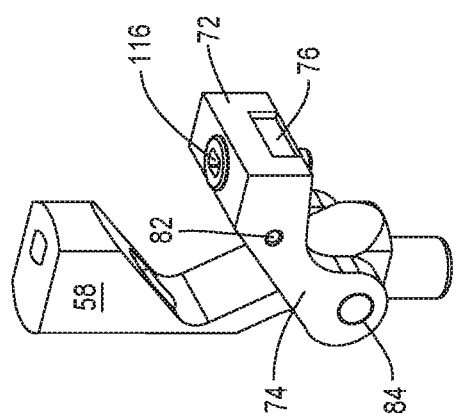
FIG. 4 is a perspective view of the saw head.
Figure 3:
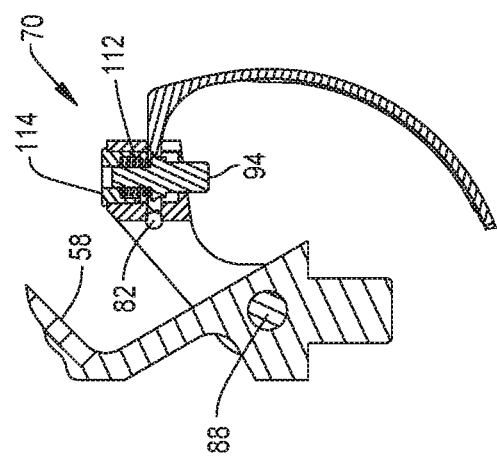
FIG. 3 is a cross sectional view of the saw head and the blade mounted to the head.
Figure 5:
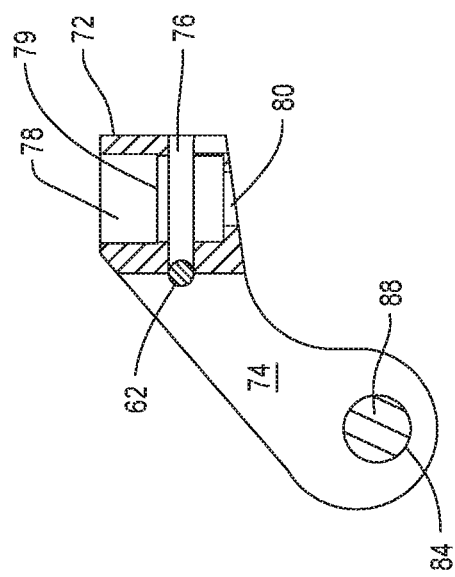
FIG. 5 is a cross sectional view of the saw head.

The saw head 70 as seen in FIGS. 3-5, is a single piece component. Saw head 70, includes a base 72 that is generally rectangular in shape. Two parallel legs 74, one identified in FIGS. 4 and 5, project outwardly from one end of the base. The head 70 is dimensioned so that legs 74 slip fit over opposed sides of the coupler 58. Each leg 74 is formed to have a rounded free end (not identified).

Saw head 70 is further formed to have a rectangular slot 76 that extends through the base 72. A circular bore 78 extends downwardly from the top of the base 72. Bore 78 intersects and extends below slot 76. The saw head 70 is further formed so, above slot 76, bore 78 has a small ledge 79. Bore 78 opens into a bore 80. Bore 80 is coaxial with and has a smaller diameter than bore 78.

The saw head 70 is formed so that each leg 74 is formed with two bores that extend side-to-side through the leg. Each leg 74 has a bore 82 located adjacent where the leg extends outwardly from the base 72. Bore 82 are coaxial. The saw head 70 is further formed so that bores 82 partially intersect the rear end of slot 76. Each leg 74 is further formed with a bore 84. Bores 84 are formed in the free ends of the legs 74 and are coaxial.

A pin 88 extends through the coupler and the leg bores 84. Pin 88 pivotally holds the head 70 to the coupler 58. Pin 62 extends through actuator slot 61 into saw head bores 82. Pin 62 extends outwardly from the leg 74 adjacent the actuator. The pin 90 is able to slide within slot 61. Collectively, the saw is designed so that that the proximal to distal movement of the actuating rod 59 and actuator 60 cause the actuator to pivot the saw head 70 about pin 88. Given that pin 62 extends between the saw head legs 74, it should be understood that the pin 62 extends across the open rear end of head slot 76.

Figure 6:
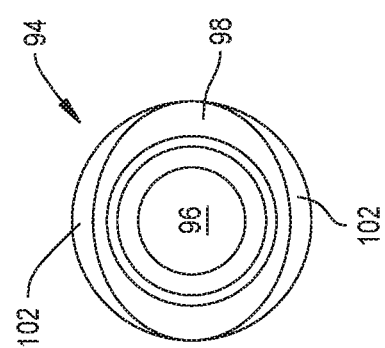
FIG. 6 is a bottom plan view of the pin moveably mounted to the saw head.
Figure 8:
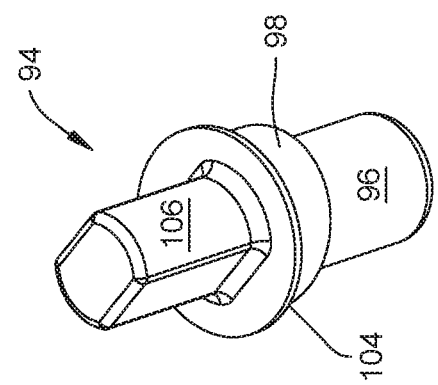
FIG. 8 is a second perspective view of the pin of FIG. 6.
Figure 7:
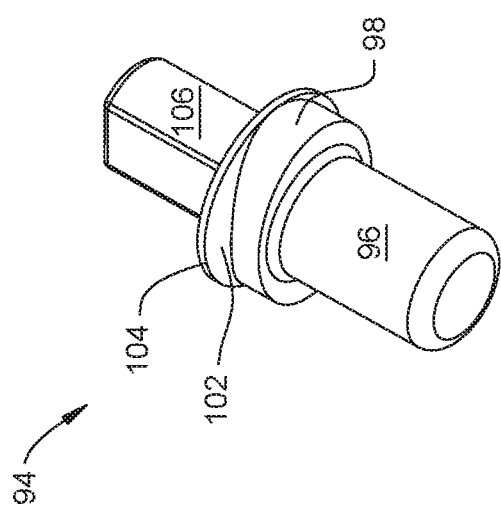
FIG. 7 is a first perspective view of the pin of FIG. 6.
Figure 10:
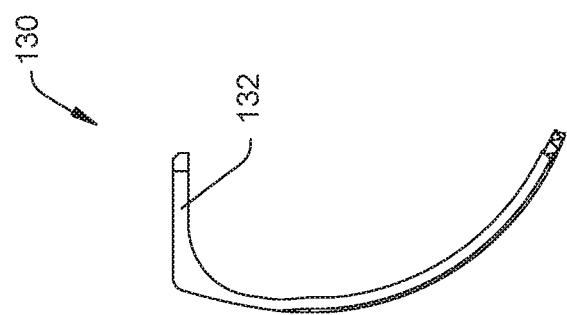
FIG. 10 is a side plan view of the saw blade.
Figure 9:
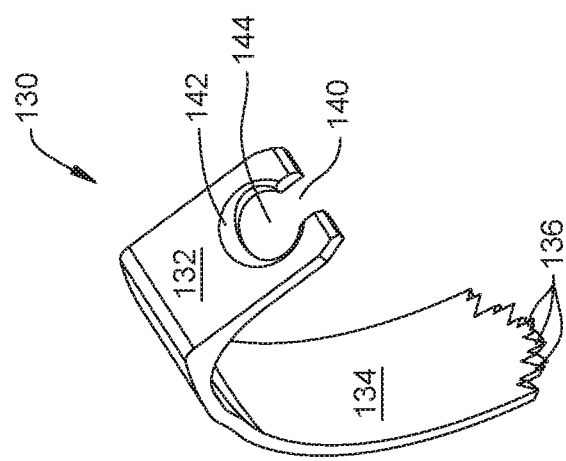
FIG. 9 is a perspective view of the sagittal saw blade of this invention.

A pin 94 is moveably mounted to the saw head base 72. Pin 94, as seen in FIGS. 6, 7 and 8, is a single piece component that has a cylindrical head 96. (In the Figures the head is seen as the bottommost component of the pin because the head 96 is the distalmost component of pin 94.) Pin head 96 is dimensioned to slip fit in the saw head bore 80. A neck 98 is located immediately above the head. Neck 98, in planes perpendicular to the longitudinal axis of the pin 94, has a cross sectional shape that is non-circular. In the illustrated version of the invention, neck has a cross sectional shape that is elliptical. It should further be understood that the major and minor axes of the neck are both longer in length than the diameter of the saw head bore 80 and pin head 96. Above the top of the neck 98 the pin has a waist 104. Waist 104 is circular in cross section. More particularly, pin 94 is formed so that the diameter of the waist 104 is equal to the length of the major axis of the neck 98.

Two diametrically opposed shoulders 102 extend outwardly from the top of the neck 98. Each shoulder 102 is symmetrically centered over one end of a line that is extension of the minor axis of the neck 98. Each shoulder extends outwardly from the neck to the waist 104. Thus where a shoulder 102 is present, the radial length of the shoulder increases moving distally to proximally along the pin 94. Each shoulder 102 thus has an outer surface that is chamfered, is tapered.

Pin 94 is further formed to have a stem 106 that extends upwardly from waist 104. Stem 106 has a shape that in cross section can be considered to be of a flattened oval. The curved end faces of stem 106 are not completely semi-circular in shape.

When saw 40 is assembled, pin 94 is mounted in the saw head so that neck 98, shoulders 102, waist 104 and stem 106 seat in head bore 78. Pin head 96 extends through bore 80. Pin neck 98 rests on the surface internal to the base that defines the interface between bores 78 and 80.

Returning to FIG. 3, it is observed that a coil spring 112 is disposed around the pin stem 106. A cap 114 is seated in bore 78. Cap 114 seats on ledge 77. The cap 114 is formed with an opening 116, identified in FIG. 4, dimensioned to receive the pin stem 106. Cap opening 116 has a cross sectional shape similar to but larger in size than the cross sectional shape of the pin stem. Collectively, the components forming the saw are dimensioned so that the stem can freely move in the cap bore 116. Not identified is void internal to the cap dimensioned to receive the spring 112.

Collectively, the components of the saw are dimensioned so that the spring 112 is compressed between the underside of the cap 114 and the circular stepped surface of the waist 104 that protrudes radially outwardly from the pin stem 106. Spring 112 thus normally urges the pin downwardly. The spring 112 is selected so the force the spring places on pin 94 can be overcome by finger force.

The blade 130 of this invention is now described by reference to FIGS. 9-12. The blade 130 is a single piece unit and is typically formed from material that can be sharpened and sterilized. Often the blade 130 is formed from stainless steel. Blade 130 is formed to have a rectangularly shaped foot 132. Foot 132 is the most proximal portion of the blade 130. The foot 132 is dimensioned to closely slip fit in the slot 76 internal to the saw head 70. A trunk 134 extends distally forward from foot 294. In the versions of the invention in which the saw functions as an acetabular cop remover, the trunk is dimensioned to extend around the outer surface of the acetabular cup 42 the blade 130 is intended to remove. Thus the trunk 134 is curved both along its longitudinal axis and lateral axis. Teeth 136 protrude outwardly from the distal end of the trunk 134. The teeth 136 are the most distal features of the blade 130.

Blade 130 is further formed so that a slot 140 extends distally forward from the proximal end of the blade foot 132. Slot 140 has a width slightly greater than the diameter of the pin head 96 and less than the length of the minor axis of the neck 98. The blade 130 is formed so that slot 140 opens up into two contiguous voids in the blade foot 132 both of which are located distal to the proximal end of the blade. A first one of these voids is opening 142. Opening 142 extends downwardly from the top planar face of the foot 132. Opening 142 is circular in shape. Opening 142 is further formed to be tapered or beveled. More particularly, as the distance from the top planar surface of the foot 132 increases, the diameter of opening 142 decreases. Opening 142 thus is defined by tapered surface 141 of the blade 130. The blade 130 is shaped so that pin shoulders 102 can seat in opening 142. Opening 142 opens into a through bore 144, the second of the two contiguous voids. Through bore 144 extends from the opening 142 to the bottom face of the blade foot 132. The blade 130 is shaped so that the dimensions of the through bore are constant along the length of the bore. The blade is further shaped so that pin neck 98 can closely seat in the through bore 144. Thus in the illustrated version of the invention the through bore 144 is elliptical in shape. The major axis of the through bore is perpendicular to the proximal to distal longitudinal axis along the blade. The major axis of the through bore has a length that is approximately 0.2 mm greater than the major axis of the pin neck 98.

The blade 130 is further shaped so that the opening 142 is not centered on the major axis of the through bore 144. In FIG. 11, dashed line 146 represents a diameter across the opening 142 perpendicular to the longitudinal axis of the blade. Dotted line 148 represents the major axis of the through bore 144. As seen by the spacing between lines 146 and 148, the center of opening 142 is located distally forward of the major axis of the through bore 148. As a consequence of this shaping of the blade 130, the portion of tapered surface 141 located towards the distal end of the blade extends further into the blade than the portion of the tapered surface 141 located towards the proximal end of the blade.

In the illustrated versions of the invention, opening 142 is circular in shape. Accordingly, in this version of the invention, the blade is constructed so that major axis 148 of through bore 144 is offset from the center of the opening 142.

Part of the process of preparing the acetabular cup remover 40 of this invention for use is the fitting of the blade 130 to head 70. To perform this process, pin head 96 is pushed upwardly. The finger force placed on the pin overcomes the force spring 112 imposes on the pin 94. Pin 94 moves along a path of travel coincident with the longitudinal axis of the pin. As a result of the pin head 96 moving upwardly, the pin is translated so that the section of the pin head adjacent neck 98 moves into head slot 76. At this time, the pin is in the load position. Blade 130 is inserted in the slot 76. More particularly, the blade 130 is generally inserted in the slot 76 so that the blade through opening 144 is approximately in registration with the pin neck 98.

The finger force used to hold the pin 94 in the load position is then released. This results in the release of the potential energy stored in the spring 112. The spring 112 acts against the pin 94 to return the pin to the run or locked position. As a result of this displacement of the pin 94, the pin neck extends through blade opening 142 into the through bore 144. Also as result of the movement of the pin, one of the pin shoulders 102 strikes blade tapered surface 141. More particularly, owing to the opening 142 and through bore 144 not being concentric, the proximally directed pin shoulder 102 strikes the proximal sections of blade tapered surface 141. This event occurs before the distally directed shoulder 102 strikes the distal section of surface 141. As a result of this asymmetric application of force on the blade, pin 94 urges the blade proximally rearward. More particularly, the blade is urged rearwardly until the proximally directed end of blade 130 abuts pin 62 integral with saw head 70. Pin 62 thus acts as a stop that prevents further movement of the blade in head slot 76. Saw 40 including blade 130 of this invention is then ready for use.

Saw 40 is used by actuating the motor 51. This results in the driver 50 oscillating the shaft 54. The pivoting of the shaft 54 results in a like pivoting of saw head 70 and, by extension blade 130. Handle 56 is urged downwardly to cause the blade to extend around the acetabular cup 42. As a result of the blade oscillating and being urged over the cup the blade teeth 136 excise the tissue surrounding the cup. The excising of this tissue makes it possible to extract the implanted acetabular cup 42.

As described above, the saw 40 and blade 130 of this invention is designed so that, owing to the arrangement of the components, the pin 94 holds the blade 130 against pin 62 integral with the saw head. Mechanically, the blade 130 can be considered to be clamped between pin 62 and pin 94. In other words, the blade is clamped along the proximal-to-distal longitudinal axis of blade foot 132. Pivot head 66, while able to rotate relative to the acetabular cup 42 has a fixed center relative to the cup 42. This means the saw head rotates around an arc that is fixed relative to the cup 42. Since blade 130 is forced against pin 62, the blade is in a fixed position relative to the saw head 70. Blade 130 therefore likewise moves around an arc that is fixed relative to acetabular cup 42. This means that the blade 130 can be shaped to move along paths of travel that, while relative close to the surface of the cup 42, do not intersect the cup. Thus the saw of this invention is designed to minimize the removal of tissue around the acetabular cup the saw is employed to remove. The minimization of this tissue removal reduces the extent to which the remaining tissue needs to heal after the procedure in which the acetabular cup remover of this invention is employed.

Further, when the saw head of this invention oscillates, the pivotally motion of the pin 94 is transferred to the blade along the non-circular interface between pin neck 98 and the adjacent non-circular surface of the saw that defines through opening 144. This reduces the extent to which the oscillatory motion of the blade 130 lags the oscillatory motion of the saw head 70. The reduction in the extent to which these two motions varies reduces the problems that occur when these motions are not substantially identical.

A further feature of the saw and blade of this invention is associated with the movement of the pin between the run/locked and load positions. As discussed there is some clearance between the pin stem 106 and the surrounding cap 114. This clearance facilitates the ability to use finger force to displace the pin from the run/locked state to the load position. A consequence of the presence of this clearance is that pin 94 is able to engage in a limited degree of rotation relative to the saw head 70. As a result of this rotation of pin 94, there may be instances in which the major axis pin neck 98 is not in alignment with the major axis of blade through opening 144. When this event occurs, and the finger force on the pin is released, the spring 112 moves the pin 94 towards the run/locked position. The downward movement of the pin 94 results in the edge around the perimeter of the pin neck 98 striking the blade tapered surface 141. As a consequence of surface 141 being tapered, the downward force is converted into a force that rotates the pin 94. The more particularly, pin 94 is rotated to cause the neck to move back to the orientation in which the major axis of the neck is in alignment with the major axis of blade through opening 150. This ensures that pin 94 fully seats in the blade 130.

Figure 14:
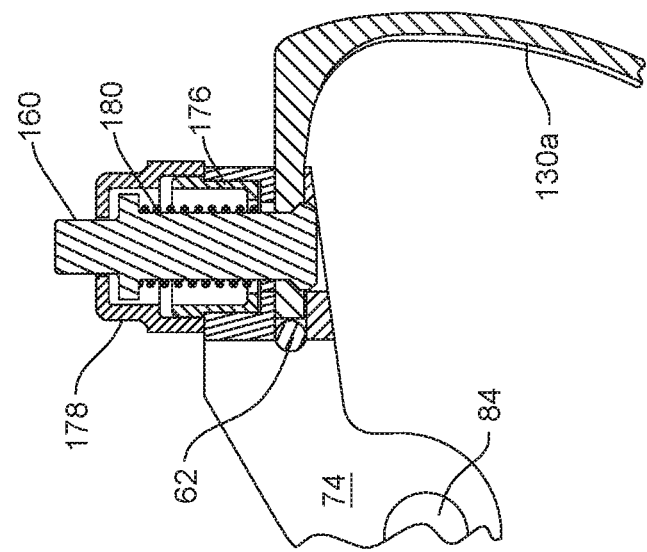
FIG. 14 is a cross sectional view of the saw and blade of FIG. 13.
Figure 13:
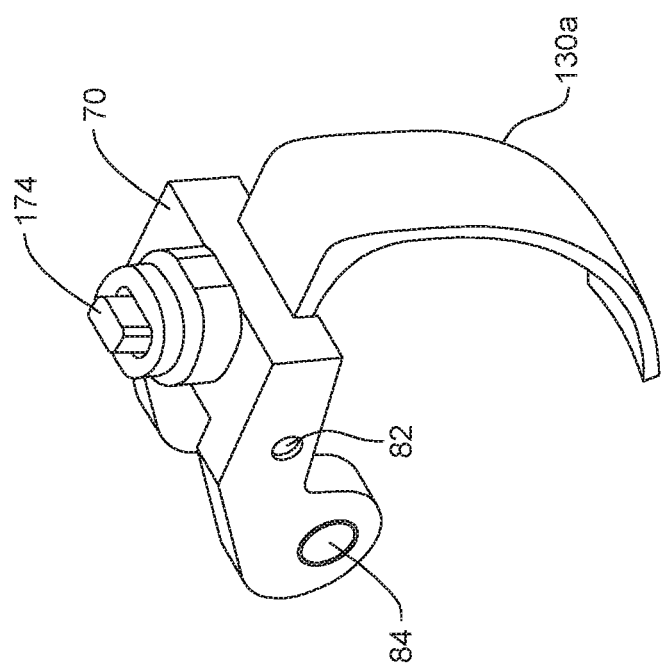
FIG. 13 is a perspective view of an alternative saw head and blade of this invention.

FIGS. 13 and 14 illustrate an alternative saw head assembly and blade 130a constructed in accordance with this invention. The saw head assembly includes the previously described saw head 70. A pin 160 is slidably disposed in the saw head 70. The pin 160 as seen in FIG. 15 includes a circularly shaped head 162. Above the head 162, pin 160 is formed with a neck 168. Neck 168 is similar to previously described pin neck 98 in that both necks are elliptical in cross sectional shape. Specifically, the major axis of neck 168 is equal to the diameter of the pin head. The minor axis of the neck 168 is less than the diameter of the pin head. Pin 160 is further shaped so that head 162 while being generally circular in shape, is formed with two symmetrically opposed strike surfaces 164. Each strike surface 164 tapers such that extending upwardly from the pin head 162 the surface extends diagonally toward an adjacent terminus of the minor axis of the neck 168.

Pin 160 is further formed to have a shaft 170 that extends upwardly from the neck 168. Shaft 170 is cylindrical in shape and has a diameter less than the length of the minor axis of the neck 168. A stop ring 172, also part of the pin 160 extends radially outwardly from the shaft 170. Pin 160 is shaped so the stop ring is spaced away neck 168. Stop ring 172 is circular in shape and has a diameter greater than that of shaft 170. A stem 174 extends upwardly from the stop ring 172 so as to be the topmost portion of pin 160. Stem 172 is similar in shape to the previously described pin stem 106.

Pin 160 is moveably mounted in saw head base 72 as seen in FIG. 14. A cup 176 is seated in base bore 78. Not identified is the hole in the base of the cup 176 through which the pin 160 extends into and through slot 76. Cup 176 projects above the saw head base. A cap 178 extends around the section of the base that extends above the base. The top of the cap 178 is formed with an opening 180 similar to opening 116 is cap 114.

When a saw with the above-described saw head assembly is put together, pin head 162 and neck 168 are generally disposed in slot 76 internal to saw head 70. Pin shaft 170 and stop ring 172 are disposed in cup 176 and cap 178. A coil spring 180 is disposed around the pin shaft 170. Spring 180 extends between either the surface internal to the head 70 that defines the base of bore 78 or the base of the cup 176 to stop ring 172. Spring 180 presses against the stop ring 172 to hold the stop ring away from head slot 76. The abutment of the stop ring against the undersurface of the top of cap 178 limits the upward movement of the pin 160.

Blade 130a is similar to blade 130. Blade 130a includes a foot 132a. Previously described trunk 134, extends downwardly from foot 134. While not seen in the Figures depicting blade 130a it us understood that previously described teeth 136 extend forward from trunk 134.

Blade 130a is formed so as to have a slot 181 extend forward from the proximal end of foot 132a. Slot 181 has a width slightly greater than the diameter of pin shaft 170. Slot 181 opens up into two contiguous void spaces. One of these void spaces is opening 184. Opening 184 extends upwardly from the underside of foot 132a. Opening 184 is in cross section circular in shape. The diameter of opening 184, like the diameter of opening 142, varies along the length of the opening. Specifically, extending upwardly from the underside face of foot 132a, the diameter of opening 184 decreases. Opening 184 is thus defined by blade tapered surface 182. Blade 130a is shaped so the section of the pin head 162 that defines surfaces 164 can seat in opening 184. Opening 184 opens into the second void space, through bore 186. Through bore 186 extends upwardly from opening 184 to the top face of the blade foot 132a. The blade 130a is shaped so through bore can closely receive pin neck 168.

Blade 130a is further formed so that opening 184 and bore 186 are not concentric. The center of opening 184 is located forward of the major axis through the bore 186.

To load blade 130a to the complementary saw assembly, finger force is applied to pin stem 174 to push the pin 160 downwardly. The finger force is sufficient to overcome the force that spring 180 applies on the pin 160 to hold the pin in the raised position, the run/locked position. As a result of the downward displacement of the pin 160, the pin shaft 170 goes into registration with saw head slot 76. Pin 160 is thus in the load position. At this time it is possible to slide blade foot 132a in the slot 76. The blade is positioned so the pin shaft extends through blade opening 184 and the through bore 186.

The finger force places on the pin 160 is then released. Spring 180 pushes upwardly on the pin 160 to return the pin to the run/locked position. This upward displacement of the pin results in the pin neck 168 seating in the through bore 186. The section of the pin head that defines surfaces 164 seats in opening 184.

The saw assembly of FIGS. 13 and 14 and blade 130a offer the same benefits as the first described saw assembly and blade 130. A difference between these two combinations is that pin 94 is pushed upwardly to move the pin 94 to the load state and pin 160 is pushed downwardly to move pin 160 to the load state.

FIG. 18 illustrates that this invention may be incorporated into what can be considered a conventional sagittal saw 202. Here a convention sagittal saw is understood to be a saw used to oscillate the planar blade 220 of FIG. 19 around an axis that extends through the plane of the blade, an axis extending in and out of the plane of FIG. 19. Saw 202 includes a pistol shaped body 204. A motor 206 represented as a dashed cylinder is disposed inside the barrel of the body. A battery 208 is shown attached to the butt end of the handgrip integral with the body 204. Battery 208 provides the charge used to energize the motor 206.

A static head 210 extends forward from the distal end of the barrel of the body 204. A blade mount 212 is rotatably mounted to head 210. Blade mount 212 is analogues in function to the previously described saw head 72. The blade mount 212 is thus the component of saw 202 to which the blade 230 is releasably mounted. In many versions of the invention the blade mount 212 includes an elongated rod like stem, not illustrated. The stem is rotatably mounted to the static head 210. The stem extends to a head portion of the blade mount. This blade mount head is the portion of the blade mount 212 disposed above the static head 210 in FIG. 18. A transmission assembly, not illustrated and not part of the present invention, extends between the motor 206 and the stem of the blade mount 212. This transmission converts the rotational motion of the shaft of motor 206 into a motion that oscillates the blade mount stem and by extension the whole of the blade mount 212 and the blade 230 mounted to the blade mount.

The head of the blade mount 212 is formed with a slot 214 for receiving the proximal end of the blade 230. While not seen, it is understood that disposed in the blade mount is a pin. This pin is similar to previously described pin 160. This pin is mounted to the blade mount such that relative to gravity, the pin head is the top most component of the pin. In some versions of the invention, this pin is slidably mounted in the stem of the blade mount 212. A clamping assembly, represented by finger lever 216, raises and lowers the pin. When the pin is lowered, the pin head presses against the blade 230. When the pin is in this state, the pin is in the run/locked state. The clamping assembly is able to raise the pin. When the pin is so raised, the pin head and neck are spaced furthest from the surface internal to the blade mount that defines the base of slot 214. When the pin is so raised, the pin shaft is in registration with slot 214. A blade 230 can be removed from or loaded into the blade mount 212. A more detailed of these features of a sagittal saw can be obtained from the previously incorporated by reference No. 8,100,912/PCT Pub. No. WO 2007/011542 as well as the now incorporated by reference U.S. Pat. No. 7,704,254/PCT Pub. No. WO 2007/030793.

The blade 230 designed for use with saw 202 as seen in FIG. 19 includes a planar body 232. Teeth 234 extend forward from the distal end of the body. Blade 230 is formed to have a slot 238 that extends forward from the proximal end of the body. Slot 238 extends to an opening 242 and a bore 244 that collectively form a top-to-bottom through hole in the blade body 232. Opening 242 is similar in shape to opening 144. Opening 242 is defined by tapered surface 240. Opening 242 extends from the face of the blade body in which the opening is formed into through bore 244. Through bore 244 is similar in shape to through bore 144. The center of opening 242 is located forward of the major axis through the through bore 244.

Blade 230 is mounted to saw 202 by setting the clamp assembly so the pin internal to the blade mount 212 is displaced. More particularly, the pin is displaced so the pin head and neck are moved upwardly, away from the surface internal to the head of the blade mount 212 that defines the base of slot 214. The blade 230 is seated in the slot so that the blade opening 242 and through opening 244 are located below the neck and head of the pin. The clamp assembly is then actuated to move the pin from the load position to the run/locked position. More specifically, the clamp assembly is actuated to lower the pin neck and head toward the base of the slot 214. As a result of this displacement of the pin, the pin neck seats in the blade through opening 244. Also as a result of this opening, the pin head surfaces analogues to strike surfaces 164 are pressed against the blade tapered surface 240. This results in the displacement of the blade along an axis angularly offset to the axis along which the pin translates. In this version of the invention this axis is typically the proximal-to-distal longitudinal axis along the length of the blade. The blade is so displaced until the blade is pushed against a static surface integral with the blade mount. The blade is thus clamped along two axes. First, as result of the head of the pin head pressing against the face of the blade, the blade is clamped along the top-to-bottom axis between the opposed faces of the blade. Here the opposed surface against which the blade is clamped is the surface on which the blade is seated. Secondly, the blade is clamped between the pin and the blade mount static surface, this clamping is along the proximal-to-distal longitudinal axis along the blade 230. In addition to the blade being clamped along these two axes, the non-circular geometry of the pin neck and complementary blade through bore 244 inhibit rotation of the blade. The pin thus holds blade 230 fast to the blade mount 212 so the blade mount and blade move as a single unit.

The above is directed to specific versions of this invention. The various features of this invention may be combined. For example, an alternative conventional sagittal saw of this invention may be constructed so that pin that to translate the pin that releasably holds the blade to the blade mount is downwardly displaced in order to move the pin from the run/locked position to the load position.

While in many versions of the invention the motor is an electrically driven motor and the motor is powered by a battery that is not a requirement of all versions of the invention. In some versions of the invention the motor may be a pneumatic or hydraulic motor. In versions of the invention in which the motor is electrically driven, the saw may be attached to a console that provides the power for actuating the motor.

Likewise, the geometric features of the components of this invention may vary from what has described. For example, there is no requirement that in all versions of the invention the blade through bore and complementary section of the pin that seats in this opening be elliptical in shape. At a minimum this bore is typically non-circular. Similarly, there is no requirement that the through bore be defined by an interior surface of the blade that is either curved or straight. In alternative versions of the invention, the through bore may different by surfaces that meet at defined, non-circular corners, vertices. Thus, it is within the scope of this invention, that the through bore be oval or a polygonal in shape. In still other versions of the invention, the through bore may be defined by a combination of interior surfaces of the blade that are both straight and curved.

Generally, regardless of the shape of through bore, in preferred versions of the invention the through bore is formed to have a major axis that is greater in length than one or more minor axes that further define the shape of the bore. In more preferred versions of the invention, the ratio of the length of the major axis of this bore to the minor axis is 1.2 to 1 or more. In still more preferred versions of the invention, the ratio of the length of the major axis of this bore to the minor axis is 1.35 to 1 or more.

Further while often preferred, there is no requirement that in all versions of the invention, the through bore be formed so that the major axis is perpendicular to the proximal-to-distal longitudinal axis along the blade. In some versions of the invention, the major axis of the through bore may be offset from the blade longitudinal axis. In some versions of the invention, the blade may be shaped so the major axis of the through bore is aligned with or parallel to the longitudinal axis along the body of the blade.

Similarly, this invention is not limited to constructions where the opening into the through bore is circular in shape. In alternative versions of the invention this opening may have other shapes. These shapes may even include shapes with one or more straight surfaces. In versions of the invention wherein this opening has straight surfaces, two of these adjacent surfaces may meet at a corner.

Likewise there is no requirement that this opening into the through bore be symmetric about an axis that extends across this opening. In an alternative version of the invention, the opening may be defined by one or more tapered surfaces that do not extend completely circumferentially around the through bore. Here the interruption due to slot 140 is ignored. The tapered surface may only subtend an arc around the center of the opening that is greater than 180°. Alternatively the tapered surface may subtend an arc of 180° or less. Thus, this opening could be defined by a tapered surface adjacent one section of the through bore and adjacent this tapered surface a surface that is extension of the inner surface of the blade that defines the through bore.

Further there is no requirement that in all versions of the invention the blade be formed so that the opening and adjacent through bore are centered on axis that are offset from each other. In versions of the invention wherein these two void spaces are located on axis that are offset, there is no requirement that in all of these versions of the invention the voids are arranged so that the axis through the opening is located distally forward of the axis through the through opening. The above arrangement is preferred if there is a reason to, upon securing the blade to the saw, urge the blade proximally. However, in alternative constructions of the invention it may be desirable to when securing the blade to the saw, urge the blade to one side. In these constructions of the invention, the blade can be designed so that the axis through the opening would be laterally spaced from the axis through the blade through bore. In still other constructions of the invention, it is useful to, upon securing the blade to the saw head, urge the blade distally forward. In these constructions of the invention, the blade can be shaped so that so that the axis through the opening is located proximal to the axis through the blade through bore.

It should be appreciated that in these and other versions of the invention, the static surface integral with the saw head against which the blade is pushed may not be the surface of a separate component, pin 62 in the primary described versions of the invention. This static surface may simply be an inner surface of the saw head that defines the perimeter of the blade slot. Alternatively, if the blade is urged forward, the static surface may be the surface of a tab integral with the saw head that protruded into the slot.

Likewise, it may not be necessary to form the blade so that that the opening and adjacent through bore are centered on axes that offset from each other. The goal of providing a blade that, when exposed to the unidirectional motion of the pin along one axis is displaced along a second axis that is angularly offset from the axis along which the pin moves can be accomplished by shaping the blade so that the taper, the chamfer, around the opening has an angle that varies around the circumference of the opening. Thus, in a version of the invention wherein it is desirable to displace the blade proximally, towards pin 62 in FIG. 5, one could provide a blade wherein the taper of the proximal section of the opening is shallower than the taper around the distal section of the opening. When the pin moves against the surfaces of the blade that define the opening, the proximally directed shoulder would strike the shallow adjacent tapered surface of the blade before the distally directed shoulder strikes the opposed opening-defining surface with the more pronounced taper. This would result in the proximally directed pin shoulder urging the blade proximally, against pin 62.

In some versions of the above describe versions of the invention, the opening into the through bore may not even be tapered around the whole of the circumference of the opening.

In some other versions of the invention, it may not be necessary to provide the blade with an opening that is either off center from the through bore or that has a varying taper. In these versions of the invention the assembly can still be designed so that when the pin moves to the run/locked position the blade is displaced along a desired axis. In these versions of the invention this movement is accomplished by shaping the pin so that shoulder surfaces are asymmetric relative to each other. Thus to provide a pin that causes proximal movement of the blade, the pin is constructed so, relative to the longitudinal axis of the pin, the proximally directed pin extends radially outwardly than the opposed distally directed pin. In this version of the invention, even though the blade opening is symmetric in shape and centered with the adjacent through bore, the proximally directed shoulder will strike the adjacent tapered surface before the opposed shoulder strikes the distally directed surface. This action would result in the desired movement of the blade along an axis that is angularly offset from the axis along with the saw head pin travels.

In some of the above-described versions of the invention of the invention, the pin may therefore only have a single shoulder with a blade-striking surface that is tapered or chamfered outwardly.

In the described versions of the invention, the saw head components and blade are designed so that when the saw head pin moves against the blade, the blade moves along an axis that is perpendicular to the axis of travel of the pin. While these movements are along axes that are angularly offset, there is no requirement that in all versions of the invention, these two axes be perpendicular.

It should be appreciated that the alternative saws of this invention would have pins with sections designed to seat in the blade through bore and opening into this bore with these alternative shapes.

Also there is no requirement that all versions include a slot that leads into the through bore and complementary opening. In versions of the invention without this slot, the saw head is constructed so the pin can seat in these blade void spaces without having to pass through the slot. Thus in these versions of the invention it may be necessary to provide a pin the free end of which is designed to seat in the blade through opening. Adjacent this section of the pin there would be surfaces similar to surface 164 that press against the surfaces of the blade that defining the opening. Alternatively, the pin can be removably attached to the blade.

Other components that coil springs may be used to bias the pin in the run/locked position against the blade.

The saws of this invention may have shapes and features different from what has been described. For example, an acetabular cup remover of this invention may not have a pivot head. Instead the most distal portion of this saw may be a plug or boss. The plug/boss rotates in a bore associated with the cup 42 being removed. In this version of the invention the acetabular cup remover and by extension the attached saw blade only rotates around the cup 42. The saw and blade do not pivot together around the cup. A standard sagittal saw of this invention may have a pencil shaped body. This type of saw is held in the web between the thumb and forefinger of the hand of the surgeon. This type of saw is typically used for small bone surgery, surgeon on the hand or foot bones.

Further while the blade is typically designed for use with a sagittal surgical saw, the features of this invention may be incorporated into other assemblies. These assemblies include saws designed to reciprocate the attached blades. Here reciprocation is understood to be back and forth movement on a path of travel that is in line with the longitudinal axis along the blade. Further the invention may be incorporated into saws that and other devices not used for medical purposes.

It is therefore the object of the appending claims to cover all such variations and modifications that come within the true spirit and scope of this invention.

What is claimed is:

1. A blade for use with a sagittal surgical saw, said blade including:
   a blade body with opposed proximal and distal ends and opposed first and second body faces and the blade body comprising a planar foot and a trunk extending distally from the planar foot;
   teeth for cutting tissue, the teeth extending forward from the distal end of the trunk;
   wherein the planar foot includes a planar first foot face comprising part of the first body face and a planar second foot face comprising part of the second body face and the planar foot is shaped to have a blade void space through the planar foot that is adjacent the proximal end of said blade body wherein the blade void space extends between the opposed first and second foot faces and the blade void space is defined by:
      an opening that extends inwardly from the first foot face, the opening at least partially defined by a surface that tapers inwardly from the first foot face so as to have a maximum diameter adjacent the first foot face; and
      an elliptical through bore that extends from the end of the opening spaced from the first foot face to the second foot face, so that the through bore defines a major axis across the through bore at a largest diameter and at least one minor axis at a smallest diameter, the largest diameter being longer in length than the smallest diameter and shorter in length than a maximum distance across the portion of the opening adjacent the first foot face.

2. The blade of claim 1, wherein the planar foot is further formed so that:
   the opening is symmetrical around an axis; and
   the through bore is formed so that the major axis of the through bore is not in registration with the axis of the opening.

3. The blade of claim 2, where the planar foot is further formed so that the major axis of the through bore is at least partially located proximal to the axis of the opening.

4. The blade of claim 1 wherein said blade body is further formed so that:
   a longitudinal axis extends between the opposed proximal and distal ends; and
   at least one of the axis of the opening or the major axis of the through bore is perpendicular to the longitudinal axis of the blade body.

5. The blade of claim 4, wherein both the axis of the opening and the major axis of the through bore are perpendicular to the longitudinal axis of the blade body.

6. The blade of claim 1, wherein the opening is circular in shape.

7. The blade of claim 1, wherein the planar foot is further formed with a slot that extends from an outer perimeter of the planar foot to the opening and the through bore, the slot having a length thereacross that is less than the length of the largest diameter of the through bore.

8. The blade of claim 1, wherein said blade body is planar in shape.

9. The blade of claim 1, wherein the trunk curves away from the planar foot.

10. The blade of claim 1, wherein the planar foot is further formed so the inwardly tapered surface that at least partially defines the blade void space opening subtends an arc greater than 180° around the opening.

11. A surgical saw assembly including:
a blade, said blade having:
  a blade body with opposed proximal and distal ends and opposed first and second body faces and the blade body comprising a planar foot and a trunk extending distally from the planar foot and the planar foot includes a planar first foot face comprising part of the first body face and a planar second foot face comprising part of the second body face;
  teeth that extend forward from the distal end of the trunk and a blade void space through the planar foot that is adjacent the proximal end, the blade body being further formed so that the blade void space has:
    an opening that extends inwardly from the first foot face of the blade body, the opening at least partially defined by a surface that tapers inwardly from the first foot so as to have a maximum diameter adjacent the first foot face; and
    an elliptical through bore that extends from the end of the opening spaced from the first foot face to the second foot face, so that the through bore defines a major axis across the through bore at a least diameter and at least one minor axis at a smallest diameter, the largest diameter being longer in length than the smallest diameter and shorter in length than a maximum distance across the portion of the opening adjacent the first foot face; and
a saw said saw having:
  a pivoting head that is formed to define a slot) shaped to receive the proximal end of said blade body and a static surface adjacent the head slot; and
  a pin disposed in the head that extends at least partially through the slot, the pin able to move along an axis and dimensioned to seat in the blade void space to removably hold the blade to the head wherein said pin is formed to have:
    a neck with a non-circular shape that is complementary the shape of the through bore in said blade body so that said neck can seat in the through bore of the blade body, and
    at least one shoulder adjacent the neck that extends outwardly from said neck and that is positioned to abut the inwardly tapered surface of said blade body so that the movement of the pin neck into the blade through bore results in the pin shoulder striking the inwardly tapered surface of the planar foot so that said blade moves along an axis angularly offset from the axis along which the pin moves in the saw head so that blade is pushed against the static surface adjacent the head slot.

12. The surgical saw assembly of claim 11, wherein;
said pivoting head of said saw is further formed so that slot extends proximally inward from a distal end of the head and the static surface at a proximal end of the slot; and
said pin and said blade are collectively shaped so that when the shoulder of the pin strikes the inwardly tapered surface that defines the opening the blade is moved proximally so the proximal end of the blade is pushed against the static surface adjacent the head slot.

13. The surgical saw assembly of claim 11, wherein:
relative to gravity, said pin is mounted to said head so as to be moved from a run state in which the inwardly tapered surface of the opening of said blade body pushes the blade against the static surface of the head slot to a load state in which blade can be removed from the slot; and
said blade is formed so that the opening in said blade body extends downwardly from a top face of the blade and the through bore extends from the opening to a bottom face of the blade wherein the top face is the first foot face and the bottom face is the second foot face.

14. The surgical saw assembly of claim 11, wherein, said pin of said saw is formed with plural shoulders that taper away from the neck.

15. The surgical saw assembly of claim 11, wherein said pin of said saw is formed so the neck is elliptical in shape.

16. The surgical saw assembly of claim 11, wherein said blade body is formed so as to have between the proximal end and said teeth a trunk that curves away from the proximal end.

17. The surgical saw assembly of claim 11, wherein said blade body is further formed so the inwardly tapered surface that at least partially defines the opening subtends an arc greater than 180° around the opening.

\* \* \* \* \*

UNITED STATES PATENT AND TRADEMARK OFFICE
CERTIFICATE OF CORRECTION

| | | |
|---|---|---|
| PATENT NO. | : 10,342,553 B2 | Page 1 of 1 |
| APPLICATION NO. | : 14/997720 | |
| DATED | : July 9, 2019 | |
| INVENTOR(S) | : Seamus Gilhooley | |

It is certified that error appears in the above-identified patent and that said Letters Patent is hereby corrected as shown below:

In the Claims

Column 17, Line 36:
Please replace "first foot so" with --first foot face so--

Signed and Sealed this
Thirty-first Day of March, 2020

Andrei Iancu
*Director of the United States Patent and Trademark Office*